(12) United States Patent
Takahashi

(10) Patent No.: US 9,299,141 B2
(45) Date of Patent: Mar. 29, 2016

(54) IMAGE ANALYSIS APPARATUS, RADIATION IMAGING APPARATUS, IMAGE ANALYSIS METHOD, AND STORAGE MEDIUM

(71) Applicant: CANON KABUSHIKI KAISHA, Tokyo (JP)

(72) Inventor: Naoto Takahashi, Sagamihara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 165 days.

(21) Appl. No.: 14/159,655

(22) Filed: Jan. 21, 2014

(65) Prior Publication Data

US 2014/0219536 A1    Aug. 7, 2014

(30) Foreign Application Priority Data

Feb. 5, 2013    (JP) .............................. 2013-020832

(51) Int. Cl.
| | |
|---|---|
| G06T 7/00 | (2006.01) |
| G06T 5/00 | (2006.01) |
| G06T 5/10 | (2006.01) |
| A61B 6/00 | (2006.01) |

(52) U.S. Cl.
CPC .............. *G06T 7/0012* (2013.01); *G06T 5/002* (2013.01); *G06T 5/10* (2013.01); *A61B 6/4291* (2013.01); *G06T 2207/10116* (2013.01)

(58) Field of Classification Search
CPC ............ G06K 9/00496; G06K 9/0057; G06K 2209/05; G06T 7/0012; G06T 2207/10116; G01T 1/2914; A61B 6/4291; A61B 6/483; A61B 6/5282

See application file for complete search history.

(56) References Cited

U.S. PATENT DOCUMENTS

| | | | |
|---|---|---|---|
| 5,028,784 A | 7/1991 | Arakawa et al. | ........... 250/237.2 |
| 5,050,198 A | 9/1991 | Honda | ............................. 378/99 |
| 5,661,818 A | 8/1997 | Gaborski et al. | .............. 382/132 |
| 7,142,705 B2 | 11/2006 | Inoue et al. | .................... 382/132 |
| 7,474,774 B2 | 1/2009 | Inoue | ............................ 382/128 |

(Continued)

FOREIGN PATENT DOCUMENTS

| | | | | |
|---|---|---|---|---|
| JP | S59-102227 | 6/1984 | ............. | G03B 41/16 |
| JP | H03-012785 | 1/1991 | ............. | G06F 15/66 |

(Continued)

OTHER PUBLICATIONS

N. Otsu, "A Threshold Selection Method from Gray-Level Histograms", *IEEE Trans. on Systems, Man, and Cybernetics*, vol. SMC-9, No. 1, pp. 62-66 (Jan. 1979).

*Primary Examiner* — Andrew W Johns
(74) *Attorney, Agent, or Firm* — Fitzpatrick, Cella, Harper & Scinto

(57) ABSTRACT

An image analysis apparatus detects a periodic signal corresponding to an arrangement of a grid, which is required to reduce scattered radiation components from an object, from an image obtained by radiation imaging using the grid. The image analysis apparatus includes: a setting unit configured to set a plurality of regions on the image; an obtaining unit configured to obtain statistic information of pixel values corresponding to each of the plurality of regions of the image based on the image; a selection unit configured to select at least one measurement region from the plurality of regions based on the statistic information; and a detection unit configured to detect the periodic signal using image data of the selected measurement region.

22 Claims, 6 Drawing Sheets

(56) References Cited

U.S. PATENT DOCUMENTS

| | | |
|---|---|---|
| 7,639,856 B2 | 12/2009 | Inoue et al. ............... 382/132 |
| 2001/0012407 A1 | 8/2001 | Takeo ...................... 382/260 |
| 2002/0024027 A1 | 2/2002 | Yamada .................... 250/584 |
| 2002/0159633 A1 | 10/2002 | Inoue ....................... 382/170 |
| 2003/0016854 A1 | 1/2003 | Inoue et al. ............... 382/132 |
| 2009/0214130 A1* | 8/2009 | Yamakita ............ A61B 6/502 |
| | | 382/260 |
| 2014/0023252 A1* | 1/2014 | Imai ...................... G06T 5/50 |
| | | 382/130 |
| 2014/0361192 A1* | 12/2014 | Imai ........................ G01T 1/16 |
| | | 250/395 |
| 2014/0363071 A1* | 12/2014 | Imai .................... G06T 7/0012 |
| | | 382/132 |

FOREIGN PATENT DOCUMENTS

| | | | |
|---|---|---|---|
| JP | H08-293020 | 11/1996 | ............. G06T 1/00 |
| JP | 2002-336223 | 11/2002 | ............. A61B 6/00 |
| JP | 3445258 | 9/2003 | ............. H04N 5/325 |
| JP | 2012-203503 | 10/2012 | ............. G06T 5/10 |

\* cited by examiner

IMAGE ANALYSIS APPARATUS, RADIATION IMAGING APPARATUS, IMAGE ANALYSIS METHOD, AND STORAGE MEDIUM

BACKGROUND OF THE INVENTION

1. Field of the Invention

The present invention relates to an image analysis apparatus, radiation imaging apparatus, image analysis method, and storage medium.

2. Description of the Related Art

Conventionally, a technique for visualizing the interior of an object by irradiating the object with a radiation represented by X-rays and imaging radiation components transmitted through the object is used.

Since the radiation generates scattered rays inside the object, the scattered rays are also imaged together with direct rays transmitted through the object. Thus, an instrument called a grid, which removes such scattered rays, is arranged between the object and radiation image-receiving surface to execute imaging. This grid removes scattered radiation components by alternately arranging a radiation shielding material such as lead and a radiation transmission material such as aluminum or carbon to have a predetermined width. Since the grid removes some direct rays passing through the radiation shielding material upon removing the scattered radiation components, it generates a periodic signal (also referred to as a grid line hereinafter) on an image.

As a method of reducing such periodic signal, a method of moving only the grid in a direction perpendicular to a line during irradiation of the radiation, and reducing line components by an integral effect is available. This method can effectively reduce the grid line, but requires mechanical control for moving the grid, resulting in a large apparatus scale, and a disadvantage in terms of cost.

In recent years, a method of reducing a periodic signal caused by the grid by image processing from imaged data has been proposed as Japanese Patent No. 3445258 by the present applicant.

A method of detecting a periodic signal caused by the grid from an image and executing processing only when the periodic signal is detected in terms of improvement of image quality is also available. For example, Japanese Patent Laid-Open No. 8-293020 discloses a method of detecting a periodic signal caused by the grid. With this method, variances in the vertical and horizontal directions are evaluated by an F-test from a plurality of measurement regions, and the presence/absence and direction of a periodic signal of the grid are detected by voting of the evaluation results.

In order to precisely detect a periodic signal of the grid from an image, it is also effective to remove an undetectable region from measurement regions in advance. For example, in Japanese Patent No. 3445258, an estimated average value of an image is calculated by random sampling, and a region less than the estimated average value (that is, an undetectable region with a low S/N) is excluded from measurement regions, thus improving the detection precision.

However, only a rejection condition of Japanese Patent No. 3445258 with reference to the estimated average value of an image is often insufficient as a condition for improving the detection precision. More specifically, when imaging is done under a condition of a small radiation dose or under a condition in which a radiation is partially shielded by a collimator, the estimated average value of an image becomes small as a whole, and a low-S/N region cannot often be appropriately excluded. In addition, high calculation cost is required since all measurement regions not less than the estimated average value are to be evaluated.

Hence, the present invention provides a technique which can improve the detection precision and can reduce calculation cost by limiting measurement regions in which a periodic signal of the grid can be detected more precisely by relative evaluation based on statistic information of measurement regions.

SUMMARY OF THE INVENTION

According to one aspect of the present invention, there is provided an image analysis apparatus for detecting a periodic signal corresponding to an arrangement of a grid, which is required to reduce scattered radiation components from an object, from an image obtained by radiation imaging using the grid, the apparatus comprising: a setting unit configured to set a plurality of regions on the image; an obtaining unit configured to obtain statistic information of pixel values corresponding to each of the plurality of regions of the image based on the image; a selection unit configured to select at least one measurement region from the plurality of regions based on the statistic information; and a detection unit configured to detect the periodic signal using image data of the selected measurement region.

According to the present invention, measurement regions in which a periodic signal of the grid can be precisely detected are limited by relative evaluation based on statistic information of measurement regions, thereby improving the detection precision and reducing calculation cost.

Further features of the present invention will become apparent from the following description of exemplary embodiments (with reference to the attached drawings).

DESCRIPTION OF THE EMBODIMENTS

An image analysis apparatus and image analysis method according to an embodiment will be described hereinafter with reference to the drawings. However, components described in the embodiment are presented only for the exemplary purpose, and the technical scope is settled by the scope of the claims but is not limited by the following individual embodiments.

Figure 1:
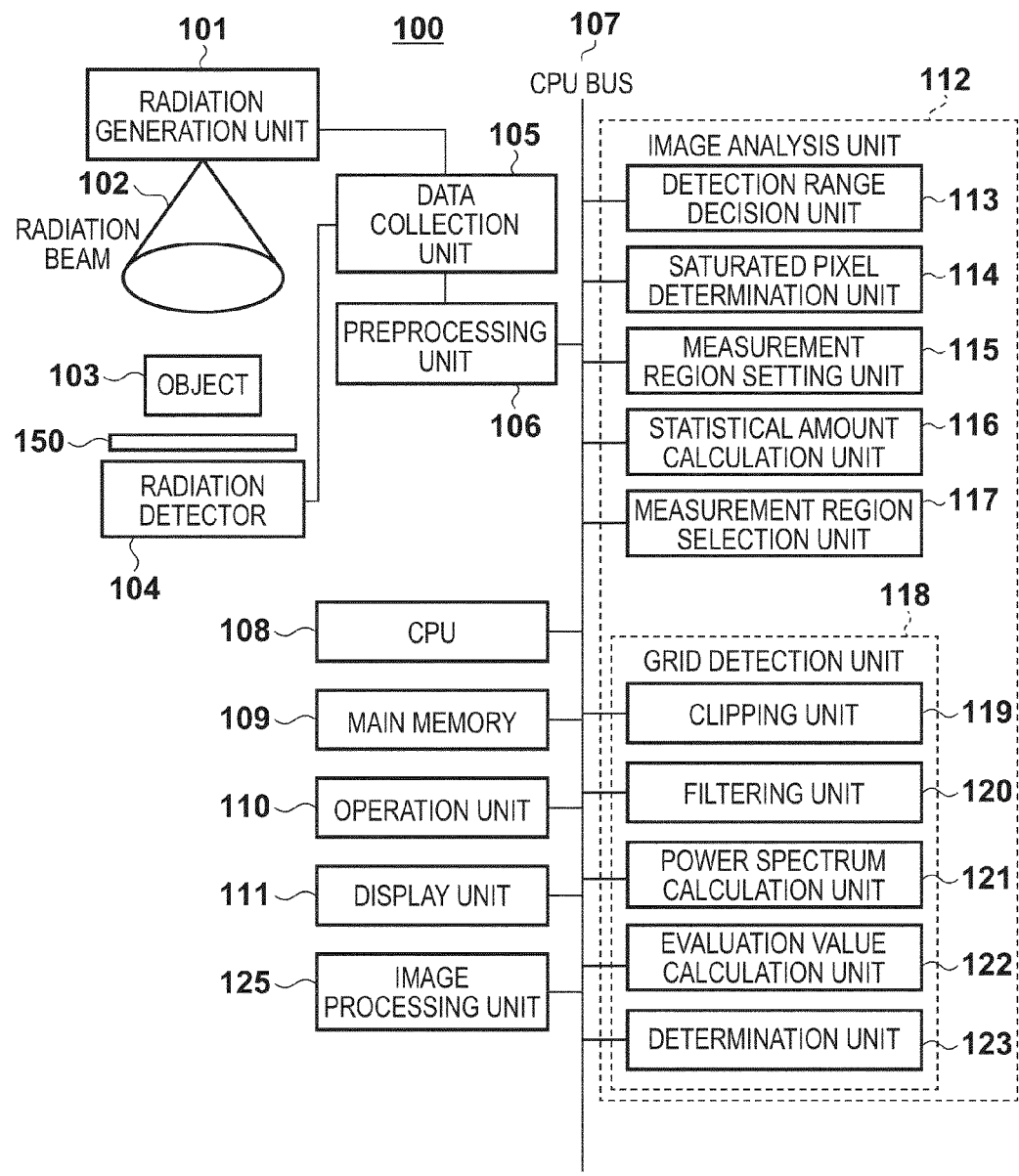
FIG. 1 is a block diagram showing an example of the overall arrangement of a radiation imaging apparatus according to an embodiment.

This embodiment is applicable to, for example, a radiation imaging apparatus 100 shown in FIG. 1. That is, the radiation imaging apparatus 100 has an image analysis function for detecting a periodic signal corresponding to an arrangement of a grid required to remove or reduce scattered radiation components in an object. The radiation imaging apparatus includes a radiation generation unit 101, radiation detector 104, data collection unit 105, preprocessing unit 106, CPU 108 which functions as a control unit, main memory 109, operation unit 110, display unit 111, image analysis unit 112, and image processing unit 125. These units are connected via a CPU bus 107 to be able to mutually exchange data. Also, a grid 150 used to remove scattered radiation components from an object 103 is arranged between the object 103 and radiation detector 104.

The image analysis unit 112 detects a periodic signal corresponding to the arrangement of the grid 150 from an image captured by the radiation detector 104. The image analysis unit 112 includes a detection range decision unit 113, saturated pixel determination unit 114, measurement region setting unit 115, statistic amount calculation unit 116, measurement region selection unit 117, and grid detection unit 118. Also, the grid detection unit 118 includes a clipping unit 119, filtering unit 120, power spectrum calculation unit 121, evaluation value calculation unit 122, and determination unit 123. These units are connected to the CPU bus 107.

In the radiation imaging apparatus 100, the main memory 109 stores various data required for processing of the CPU 108, and also functions as a working memory of the CPU 108. The CPU 108 executes operation control and the like of the overall apparatus according to operations from the operation unit 110 by using the main memory 109. Thus, the radiation imaging apparatus 100 operates as follows.

When the user inputs an imaging instruction via the operation unit 110, the CPU 108 transmits this imaging instruction to the data collection unit 105. Upon reception of the imaging instruction, the CPU 108 controls the radiation generation unit 101 and radiation detector 104 to execute radiation imaging.

In the radiation imaging, the radiation generation unit 101 irradiates the object 103 with a radiation beam 102. The radiation beam 102 irradiated from the radiation generation unit 101 is transmitted through the object 103 while being attenuated, and reaches the radiation detector 104. The grid 150 removes scattered radiation components from the object 103. Then, the radiation detector 104 outputs a signal according to a reached radiation intensity. Note that a human body is used as an example of the object 103. Hence, the signal output from the radiation detector 104 is data obtained by capturing an image of the human body. Note that the radiation detector 104 is not limited to of a fixed type, but may be of a portable type. For example, when the radiation detector 104 of a portable type is used, a relative position between the object 103 and grid 150 can be easily adjusted according to an portion to be imaged of the object 103.

The data collection unit 105 converts the signal output from the radiation detector 104 into a predetermined digital signal, and supplies that digital signal to the preprocessing unit 106 as image data. The preprocessing unit 106 applies preprocessing such as offset correction and gain correction to the image data supplied from the data collection unit 105. The image data which has undergone the preprocessing by the preprocessing unit 106 is sequentially transferred to the main memory 109 and image analysis unit 112 via the CPU bus 107 under the control of the CPU 108.

The image analysis unit 112 detects a periodic signal corresponding to the arrangement of the grid 150 from the transferred image data. The image processing unit 125 executes reduction processing of the periodic signal when the periodic signal of the grid 150 is detected from the image data. Also, the image processing unit 125 executes other kinds of image processing. The image processing unit 125 can execute general tone conversion processing, sharpening processing, and the like as other kinds of image processing, and image processing results are output to a printer (not shown), the display unit 111, and the like. The display unit 111 displays an image which has undergone the periodic signal reduction processing by the image processing unit 125. With the aforementioned processing, a series of imaging operations are complete.

The operation of the image analysis unit 112 as a characteristic feature of this embodiment in the radiation imaging apparatus 100 with the aforementioned arrangement will be described in detail below with reference to the flowcharts shown in FIGS. 2 and 3.

Image data obtained by the preprocessing unit 106 is transferred to the image analysis unit 112 via the CPU bus 107. The detection range decision unit 113 of the image analysis unit 112 decides a rough detection range required to detect a periodic signal (to be also referred to as a grid line hereinafter) corresponding to the arrangement of the grid 150 by executing steps S201 and S202. This detection range includes a radiation irradiation region, with which the object is irradiated. On the radiation image-receiving surface, a grid line is observed as a shade corresponding to the arrangement of the grid 150. With the processing of the image analysis unit 112, a periodic signal corresponding to the arrangement of the grid 150 is precisely detected, and when the periodic signal of the grid 150 is detected from image data, the reduction processing of the periodic signal (grid line) is executed by the processing of the image processing unit 125. The reduction processing of the periodic signal (grid line) can reduce unnaturalness for an observer of a radiation image due to the presence of the grid line on the radiation image as much as possible.

In this case, in the radiation imaging, it is a common practice to limit an irradiation field so as to irradiate only a required region with a radiation for the purpose of suppression of exposure of a region outside the required region with a radiation, and an image includes a region which is not irradiated with a radiation. Since this region which is not irradiated with a radiation (so-called unexposed region) includes nearly no signal components, it is difficult to detect the grid 150. Hence, a range obtained by roughly excluding this region is set as a detection range.

In step S201, the detection range decision unit 113 of the image analysis unit 112 calculates a threshold required to decide a detection range irradiated with a radiation. Note that the threshold decision method is not particularly limited. In this embodiment, the threshold required to separate into a radiation irradiated region and non-irradiated region is calculated by an Otsu's method based on discriminant criteria. In this method, an inter-class variance when an image is separated into two classes is calculated, and a pixel value corresponding to a maximum inter-class variance is decided as an optimal threshold required to separate a foreground region (radiation irradiated region) and a background region (radiation non-irradiated region).

Note that the Otsu's method is a known technique, and a detailed description thereof will not be given. For further details of the Otsu's method, for example, see [Nobuyuki Otsu: "A Threshold Selection Method from Gray-Level Histograms, IEEE Trans. on Systems, Man, and Cybernetics", Vol. SMC-9, No. 1, pp. 62-66, 1979.]

Figure 4:
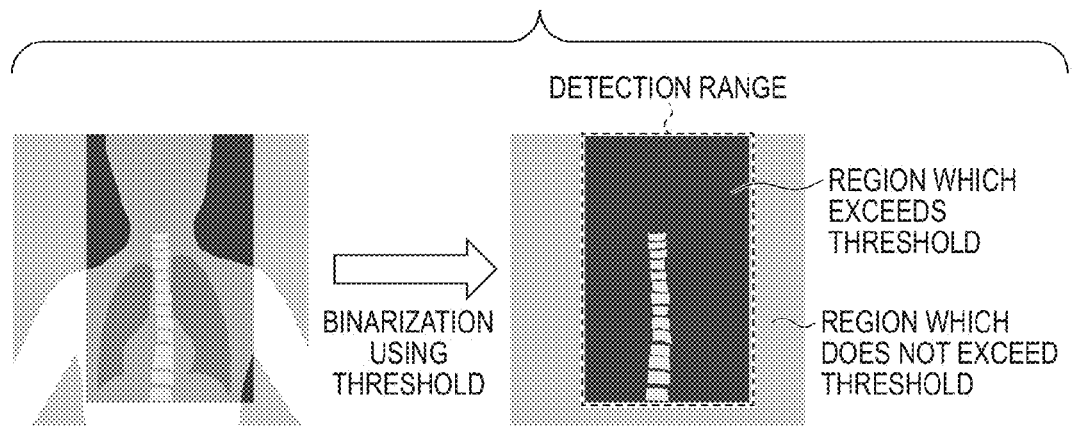
FIG. 4 is an exemplary view for explaining a detection range.

Next, in step S202, the detection range decision unit 113 of the image analysis unit 112 decides a detection range based on the calculated threshold. In this case, a region exceeding the threshold is considered as a region irradiated with a radiation (detection range), and a circumscribed rectangular region of the region exceeding the threshold is set as a detection range, as shown in FIG. 4. Note that since the circumscribed rectangular region is set as the detection range in this embodiment, even when the region irradiated with a radiation partly includes a region which does not exceed the threshold, the region irradiated with a radiation can be set as the detection range.

Next, in step S203, the saturated pixel determination unit 114 of the image analysis unit 112 calculates a threshold required to determine whether or not a pixel is saturated. Note that the threshold decision method is not particularly limited. This embodiment uses, for example, a method of Japanese Patent Laid-Open No. 2002-336223 which has already been proposed by the present applicant. More specifically, a histogram of the detection range is approximated by a polygonal line including two straight lines, and a pixel value corresponding to a break point of the approximated polygonal line is set as a threshold required to separate into a pixel saturated region and non-saturated region. Note that since an output value when a pixel is saturated can be roughly estimated depending on a sensor upon setting in advance a fixed threshold for each sensor, the need for the estimation processing can be obviated, thus reducing the processing load.

Next, the measurement region setting unit 115 sets a plurality of measurement regions in the detection range calculated by the detection range decision unit 113 by executing steps S204 and S205. Note that "measurement" is that of statistic information (statistic amount) to be described below, and a partial region in the detection range used to measure the statistic information will be referred to as a measurement region hereinafter. In this embodiment, a measurement region can be, for example, a linear partial region having a width of one pixel (to be referred to as "line" hereinafter) or a rectangular region having a width of two pixels or more. In the following description, the case will be exemplified wherein a line is used as a measurement region. Note that a measurement region is not limited to a line or rectangular region, and various partial region shapes and their modifications required to detect the grid 150 can be used.

Figure 5A:
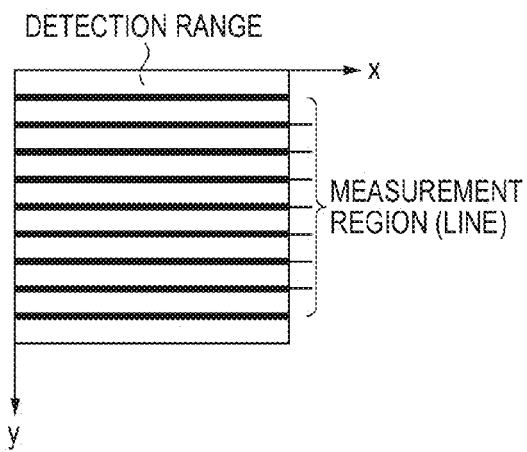
FIGS. 5A and 5B are exemplary graphs for explaining settings of measurement regions.
Figure 5B:
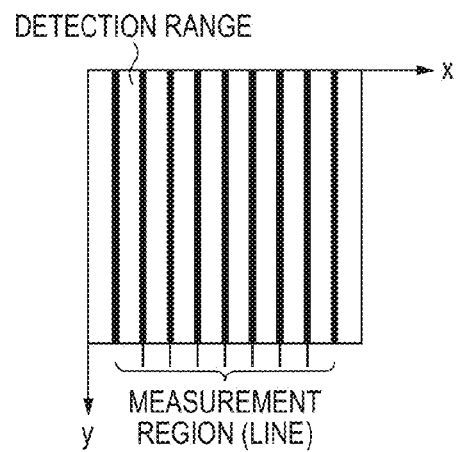

In step S204, a plurality of lines are set at equal intervals with respect to a horizontal direction (for example, a first direction) of the detection range, as shown in FIG. 5A. Also, in step S205, a plurality of lines are set at equal intervals with respect to a vertical direction (for example, a second direction perpendicular to the first direction) of the detection range, as shown in FIG. 5B. Note that in this embodiment, in consideration of the subsequent Fourier transformation, when a line length (the number of samples) is not the power of 2 (n-th power of "2" (n is a positive integer)), the number of data points at the two ends of the line is truncated so that the line length matches the power of 2.

In this case, the number of lines to be set can be arbitrarily set, and for example, 100 lines may be set at equal intervals. Note that line intervals are not limited to equal intervals. For example, by combining processing for correcting a statistic amount between neighboring lines according to an interval, arbitrary intervals may be set. Also, of the detection range, all regions (all lines) may be set as measurement regions.

Next, the statistic amount calculation unit 116 of the image analysis unit 112 calculates statistic amounts of the respective lines set by the measurement region setting unit 115 by executing steps S206 and S207. More specifically, letting s[n] be one set line data, a statistic amount E is calculated using:

$$E = \sum_{n=0}^{N-1} s[n] \cdot I(s[n]), \quad I(x) = \begin{cases} 1, & x < TH \\ 0, & x \geq TH \end{cases} \quad (1)$$

where N is the number of samples of line data, that is, the number of lines as samples set by the measurement region setting unit 115. TH is the threshold calculated by the saturated pixel determination unit 114.

The statistic amount E is calculated for all the lines set in the horizontal and vertical directions.

The statistic amount E calculated by the above equation assumes a larger value for a line which includes few saturated pixels, and assumes a larger total pixel value (large reached dose). That is, the statistic amount E assumes a smaller value for a line which partially does not include a periodic signal of the grid 150 due to saturation and in which the periodic signal is difficult to be detected or for a line having a low S/N and in which the periodic signal of the grid 150 is difficult to be detected. Using this statistic amount E, a line in which the periodic signal of the grid 150 can be detected more precisely can be evaluated.

Note that as the statistic information, this embodiment calculates a sum total value of pixel values except for saturated pixels as the statistic amount E. However, the present invention is not limited to this. For example, in place of the sum total value, other kinds of statistic information such as an average value, mode, order statistic value, variance, or standard deviation can be used.

Next, the measurement region selection unit 117 selects at least one (predetermined number) measurement region as that in which the periodic signal of the grid 150 can be detected more precisely from the plurality of measurement regions set by the measurement region setting unit 115 by executing steps S208 and S209. This embodiment will explain an example in which measurement regions of the predetermined number M are to be selected as measurement regions in the vertical and horizontal directions. Note that the gist of this embodiment is not limited to this example, and measurement regions of different numbers may be selected respectively in the vertical and horizontal directions.

The measurement region selection unit 117 compares the statistic amounts E of the respective measurement regions calculated by the statistic amount calculation unit 116, and selects top M measurement regions in descending order of values of the statistic amount E. Note that in this embodiment, since the lines in the horizontal and vertical directions are independently set, the statistic amounts E of the plurality of measurement regions set in the horizontal direction are compared first to select top M measurement regions in descending order of values of the statistic amount E in step S208. Also, the statistic amounts E of the plurality of measurement regions set in the vertical direction are compared to select top M measurement regions in descending order of values of the statistic amount E in step S209.

As described above, since the statistic amount E corresponds to a region which allows easier detection of the grid 150 as it assumes a larger value, top M regions are selected in descending order of values, undetectable regions of the grid 150 are excluded in advance from the measurement regions, thus improving the detection precision. By limiting the measurement regions to the predetermined number M, processing cost required for the subsequent processes can be reduced. Note that the predetermined number M need only be empirically decided in consideration of the detection precision and processing cost, and for example, M=10.

Figure 3A:
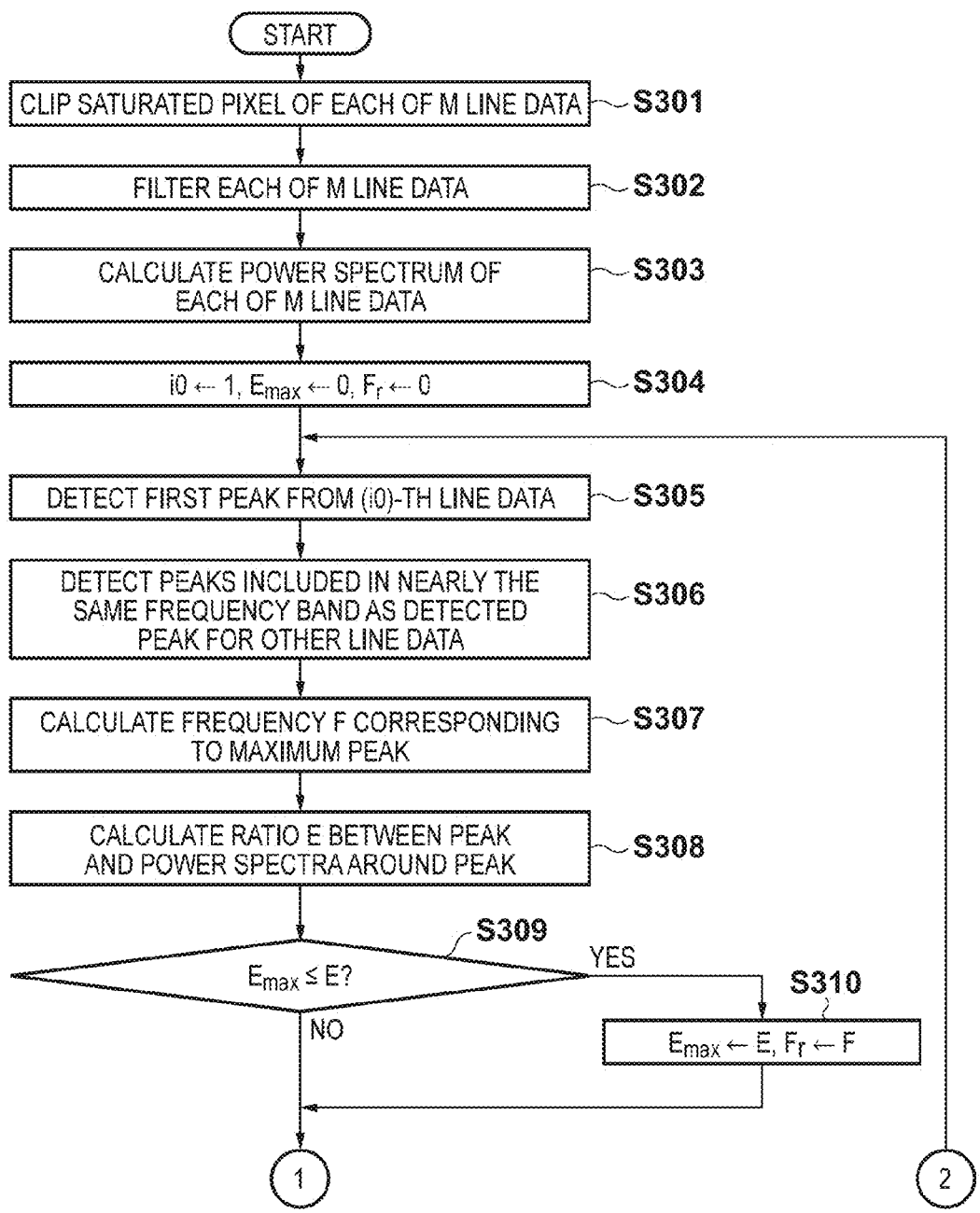
FIGS. 3A and 3B are flowcharts showing the processing sequence of a grid detection unit according to the embodiment.
Figure 3B:
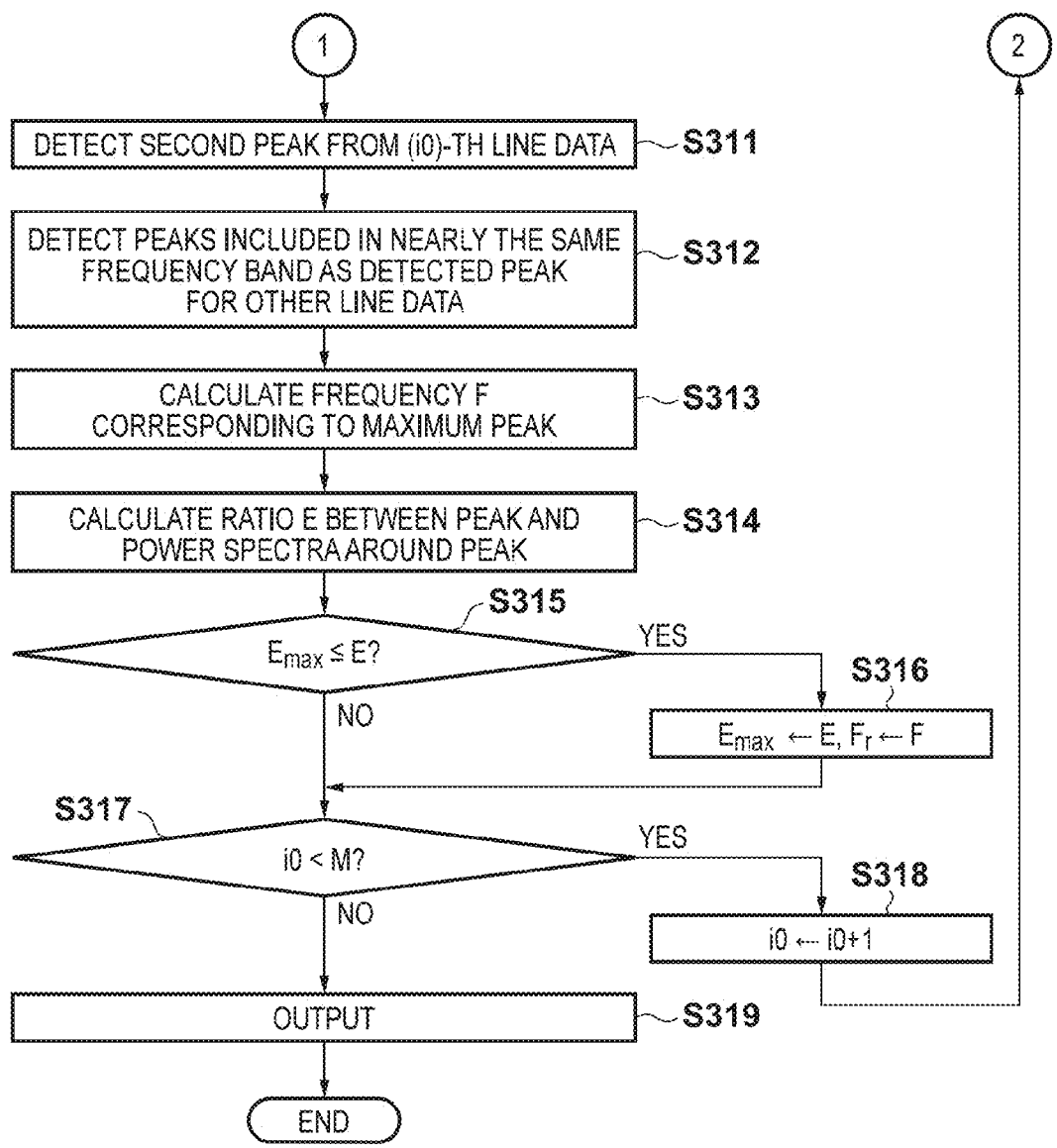

Next, the grid detection unit 118 calculates evaluation values from the selected measurement regions in the horizontal and vertical directions by executing steps S210 and S211. Note that steps S210 and S211 execute the same processing although input measurement regions are different. More specifically, processing according to the flowchart shown in FIGS. 3A and 3B is executed to have input M measurement regions, that is, M line data as inputs. The calculation processing of the evaluation values will be described in detail below with reference to the flowchart of FIGS. 3A and 3B.

In step S301, the clipping unit 119 of the grid detection unit 118 clips M line data for the purpose of removing correction noise caused by saturation. The M line data are input according to:

$$s1_i[n] = \begin{cases} s0_i[n], & n < TH \\ TH, & n \geq TH \end{cases} \quad (2)$$

where TH is the threshold calculated by the saturated pixel determination unit 114.

More specifically, letting $s0_i[n]$ be i-th line data of the input M line data, the equation above calculates clipped line data $s1_i[n]$, which is calculated for all the line data. When line data of the selected measurement region includes a saturated pixel, a pixel value of which is saturated, the clipping unit 119 converts the pixel value of that pixel to a fixed value (threshold TH), and sets it as data used in filtering. On the other hand, when line data does not include any saturated pixel, the clipping unit 119 sets pixel values of respective pixels in the line data as data used in filtering. The aforementioned processing by the clipping unit 119 will be referred to as clipping processing hereinafter.

Next, in step S302, the filtering unit 120 of the grid detection unit 118 extracts periodic signal components of the grid 150 by filtering. More specifically, letting $f_g$ (rad/sample) be a grid frequency on an image, all line data are filtered using an FIR filter h of N-th order, which is calculated by:

$$h[i] = \begin{cases} \dfrac{g\left(i - \dfrac{N}{2}\right)}{\mu} - 1, & i = \dfrac{N}{2} \\ \dfrac{g\left(i - \dfrac{N}{2}\right)}{\mu}, & \text{otherwise} \end{cases}, \quad i \in \{0, 1, 2, \ldots, N\} \quad (3)$$

$$\mu = \sum_{i=0}^{N} g\left(i - \dfrac{N}{2}\right), \quad g(x) = e^{\dfrac{-x^2}{2\sigma^2}}, \quad \sigma = \dfrac{3}{f_g}, \quad N = 2\lceil 3\sigma \rceil$$

Figure 6:
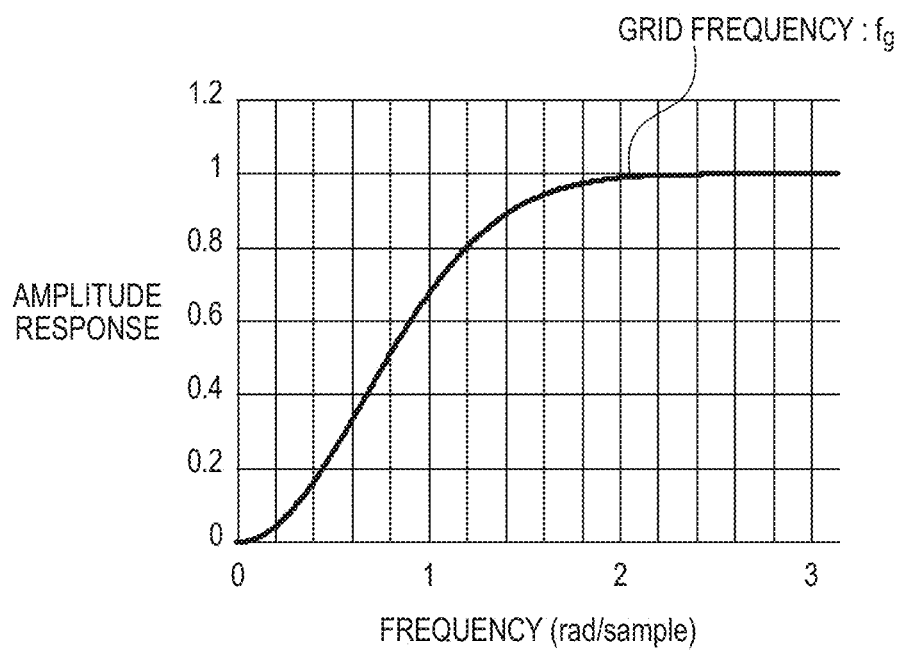
FIG. 6 is an exemplary graph for explaining an amplitude response of a filter.

In this case, FIG. 6 shows an amplitude response of a filter given by the above equation when $f_g$ is 2.0 (rad/sample). As shown in FIG. 6, the filter in this case is a high-pass filter which passes through frequencies of 2.0 (rad/sample) or more. Using this filter, image components mainly including low-frequency components can be removed while leaving periodic signal components of the grid 150. Thus, a detection error of the grid 150 caused by image components can be suppressed.

Note that the grid frequency $f_g$ (rad/sample) is decided based on the density of the grid to be used (the number of arranged lines of the grid per unit length) and the pixel pitch of the detection unit (sensor) used in the radiation imaging. More specifically, letting D (lines/cm) be the density of the grid to be used, and S (mm) be the pixel pitch, the grid frequency $f_g$ (rad/sample) can be calculated by:

$$f_g = 2\pi \cdot \left| \dfrac{D \cdot S}{10} - n \right| \quad (4)$$

for n is an integer which satisfies a conditional formula given by:

$$0 \leq f_g \leq \pi \quad (5)$$

In this case, the density of the grid to be used is given in each environment, and that value can be set in advance. Note that the grid density including a margin may be set in consideration of manufacturing variations of the grid, an enlargement factor at the time of installation, and the like. When a plurality of grids with different densities are to be used, if a smallest value of grid frequencies calculated using the above equation is set as the grid frequency $f_g$, the filter can function as a high-pass filter which passes through frequencies of all the grids to be used, and can cope with all the grid frequencies.

Next, in step S303, the power spectrum calculation unit 121 of the grid detection unit 118 calculates a normalized power spectrum using linear discrete Fourier transformation for each of line data filtered by the filtering unit 120. More specifically, letting $s_i[n]$ be i-th line data of the M filtered line data, the power spectrum calculation unit 121 calculates a power spectrum $P_i[n]$ by:

$$P_i[k] = \dfrac{1}{N^2} \cdot \left| \sum_{n=0}^{N-1} s_i[n] \cdot e^{-\dfrac{2\pi \cdot j}{N} \cdot k \cdot n} \right|^2, \quad k \in \{0, 1, 2, \ldots, N-1\} \quad (6)$$

where j is an imaginary number, and N is the number of samples of line data.

The power spectrum calculation unit 121 calculates power spectra for all the line data. In this embodiment, the number of samples of line data is the power of 2, and a calculation using fast Fourier transformation is made.

Figure 7:
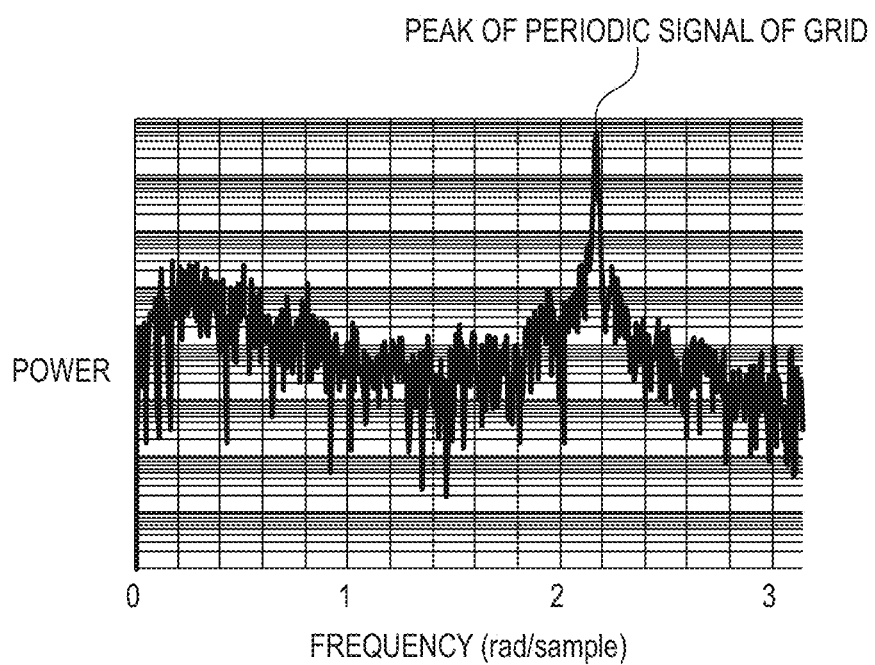
FIG. 7 is an exemplary graph for explaining a power spectrum of a periodic signal of a grid.

Note that in the power spectrum of line data in a direction perpendicular to the grid line, a peak of the periodic signal of the grid appears, as shown in FIG. 7. Hence, by detecting this peak, the presence/absence of a line of the periodic signal of the grid, a direction of the line, and a frequency of the periodic signal can be calculated.

Next, the evaluation value calculation unit 122 of the grid detection unit 118 calculates an evaluation value required to judge the presence/absence of the periodic signal corresponding to the grid 150 from the peak of the power spectrum by executing steps S304 to S318.

Initially, in step S304, the evaluation value calculation unit 122 initializes a number i0 of line data to be processed to "1", an evaluation value $E_{max}$ to "0", and a grid frequency $F_r$ to "0".

Next, in step S305, the evaluation value calculation unit 122 detects a first peak from a power spectrum $P_{i0}[k]$ of the set (i0)-th line data. In the power spectrum $P_{i0}[k]$ of the line data, a point $km_{i0}$ which assumes a maximum value within a frequency range from $f_g$ to $\pi$ (rad/sample), that is, a k range from $f_g N/2\pi$ to $N/2$ (N is the number of samples of line data), and a power spectrum $P_{i0}[km_{i0}]$ are calculated.

Next, in step S306, the evaluation value calculation unit 122 detects first peaks from power spectra $P_i[k]$ (i≠i0) of line data other than the set (i0)-th line data. In this case, when the peak detected from the (i0)-th line data is that of the periodic signal of the grid 150, peaks are present in roughly the same frequency band in the power spectra $P_i[k]$ ($i \neq i0$) of other line data. Hence, points $km_i$ each of which assumes a maximum value within a range of $km_{i0} \pm \Delta k$, and power spectra $P_i[km_i]$ at that time are calculated.

Note that $\Delta k$ can be arbitrarily set in consideration of in-plane variations of the grid density and the like. For example, in this embodiment, $\Delta k$ is set to be N/40 (N is the number of samples of line data).

In step S307, the evaluation value calculation unit 122 sets a frequency $2\pi km_i/N$ corresponding to the point $km_i$ which assumes the maximum value of the calculated M first peaks $P_i[km_i]$ (i=1, 2, 3, ..., M) as a grid frequency $F_r$ (rad/sample).

Next, in step S308, the evaluation value calculation unit 122 calculates an evaluation value E from the calculated M first peaks $P_i[km_i]$ (i=1, 2, 3, ..., M). More specifically, letting $km_i$ be a peak point of the i-th line data, the evaluation value calculation unit 122 calculates evaluation values $E_i$ for all the line data by:

$$E_i = \frac{P_i[km_i - 1] + P_i[km_i] + P_i[km_i + 1]}{\frac{1}{2\Delta k + 1} \cdot \sum_{k=-\Delta k}^{k=\Delta k} P_i[km_i + \Delta k]} \quad (7)$$

In this step, the evaluation value calculation unit 122 calculates an evaluation value using a ratio of the peak of the power spectrum to the power spectra around this peak.

Next, the evaluation value calculation unit 122 obtains an average value of the calculated M evaluation values Ei to calculate one average evaluation value E. The average evaluation value E Is given by:

$$E = \frac{1}{M} \cdot \sum_{i=1}^{M} E_i \quad (8)$$

Note that the evaluation value $E_i$ obtained by equation (7) represents a ratio between a sum of power spectrum values of three points to have a peak point as the center, and power spectra around the peak point as the center (an average value of power spectra within a $\pm \Delta k$ range). The evaluation value $E_i$ assumes a larger value as a peak becomes larger than surrounding power spectra. Also, the average evaluation value E obtained by equation (8) is an average of the evaluation values $E_i$ calculated from all the line data. When a large peak is generated on power spectra of all the line data like the periodic signal of the grid 150, the average evaluation value E assumes a large value. By evaluating this value, the presence/absence of the periodic signal corresponding to the grid 150 can be judged.

Note that this embodiment uses the sum of the power spectrum values of the three points having the peak point as the center to calculate the evaluation value $E_i$. However, the present invention is not limited to this. For example, only the power spectrum value of the peak point may be used. Also, this embodiment uses the average value of the power spectra within the $\pm \Delta k$ range having the peak point as the center to calculate the evaluation value $E_i$. However, the present invention is not limited to this. For example, a median value of the power spectra within the $\pm \Delta k$ range may be used. Also, $\Delta k$ can be arbitrarily set. For example, in this embodiment, $\Delta k$ is set to be N/10 (N is the number of samples of line data).

Next, in step S309, the evaluation value calculation unit 122 compares the calculated average evaluation value E with a maximum value $E_{max}$ of the evaluation values $E_i$. If the average evaluation value E is equal to or larger than the maximum value $E_{max}$ of the evaluation values $E_i$ (YES in step S309), the evaluation value calculation unit 122 judges in step S310 that the newly calculated average evaluation value E is a more reliable value as an evaluation value of the grid. Then, the evaluation value calculation unit 122 updates the value of the maximum value $E_{max}$ by that of the average evaluation value E, and updates the grid frequency $F_r$ based on the maximum value $E_{max}$ by a grid frequency F based on the average evaluation value E.

On the other hand, if it is determined in step S309 that the average evaluation value E is smaller than the maximum value $E_{max}$ of the evaluation values $E_i$ (NO in step S309), the evaluation value calculation unit 122 advances the process to step S311.

Next, in step S311, the evaluation value calculation unit 122 detects a second peak from the power spectrum $P_{i0}[k]$ of the set (i0)-th line data. In this step, an evaluation value is calculated for the second peak in the same manner as in the first peak in consideration of a case in which the first peak calculated in the previous stage is not caused by the periodic signal of the grid 150, for example, a wrong peak caused by a disturbance or the like is detected. More specifically, in the power spectrum $P_{i0}[k]$ of the line data, a point $km_{i0}$ which assumes a maximum k value within a frequency range from $f_g$ to n (rad/sample), that is, a range obtained by excluding the frequency range ($km_{i0} \pm \Delta k$) of the first peak from the range from $f_g N/2\pi$ to N/2 (N is the number of samples of line data), and a power spectrum value $P_{i0}[km_{i0}]$ are calculated. That is, the evaluation value calculation unit 122 calculates an evaluation value further using a ratio between a peak (second peak) which is present in a frequency band separated by a predetermined frequency or more from the first peak, and power spectra around the peak present in this frequency band.

Note that $\Delta k$ can be arbitrarily set. For example, in this embodiment, $\Delta k$ is set to be N/40 (N is the number of samples of line data).

Next, the evaluation value calculation unit 122 executes steps S312 to S314 for the calculated second peak. The processes of steps S312 to S314 have the same processing contents as those of steps S306 to S308. Then, in step S315, the evaluation value calculation unit 122 compares the calculated average evaluation value E with a maximum value $E_{max}$ of the evaluation values $E_i$. If the average evaluation value E is equal to or larger than the maximum value $E_{max}$ of the evaluation values $E_i$ (YES in step S315), the evaluation value calculation unit 122 judges in step S316 that the newly calculated average evaluation value E is a more reliable value as an evaluation value of the grid 150. Then, the evaluation value calculation unit 122 updates the value of the maximum value $E_{max}$ by that of the average evaluation value E, and updates the grid frequency $F_r$ based on the maximum value $E_{max}$ by a grid frequency F based on the average evaluation value E.

On the other hand, if it is determined in step S315 that the average evaluation value E is smaller than the maximum value $E_{max}$ of the evaluation values $E_i$ (NO in step S315), the evaluation value calculation unit 122 advances the process to step S317.

If i0<M in step S317, that is, if the evaluation value calculation unit 122 determines that evaluation values have not been calculated yet with reference to all the line data (YES in step S317), it increments the value i0 by "1" (step S318). Then, the evaluation value calculation unit 122 returns the process to step S305 to execute the processes in step S305 and subsequent steps for all the line data.

On the other hand, if i0≥M in the determination of step S317, that is, if the evaluation value calculation unit 122 determines that evaluation values have been calculated with reference to all the line data (YES in step S317), it advances the process to step S319.

Then, in step S319, the evaluation value calculation unit 122 outputs the final evaluation value $E_{max}$ and grid frequency $F_r$. The output of the evaluation value calculation unit 122 can be displayed on the display unit 111 via the CPU bus 107.

The method of calculating the evaluation value $E_{max}$ and grid frequency $F_r$ from the M measurement regions, that is, M line data has been explained using the flowchart shown in FIGS. 3A and 3B. As described above, the evaluation value $E_{max}$ is a value when the average value of ratios between peaks calculated from the first and second peaks and power spectra around the peaks with reference to all the line data is maximum. Therefore, the evaluation value $E_{max}$ exhibits a large value when a large peak is generated on power spectra of all the line data like the periodic signal of the grid.

Figure 2:
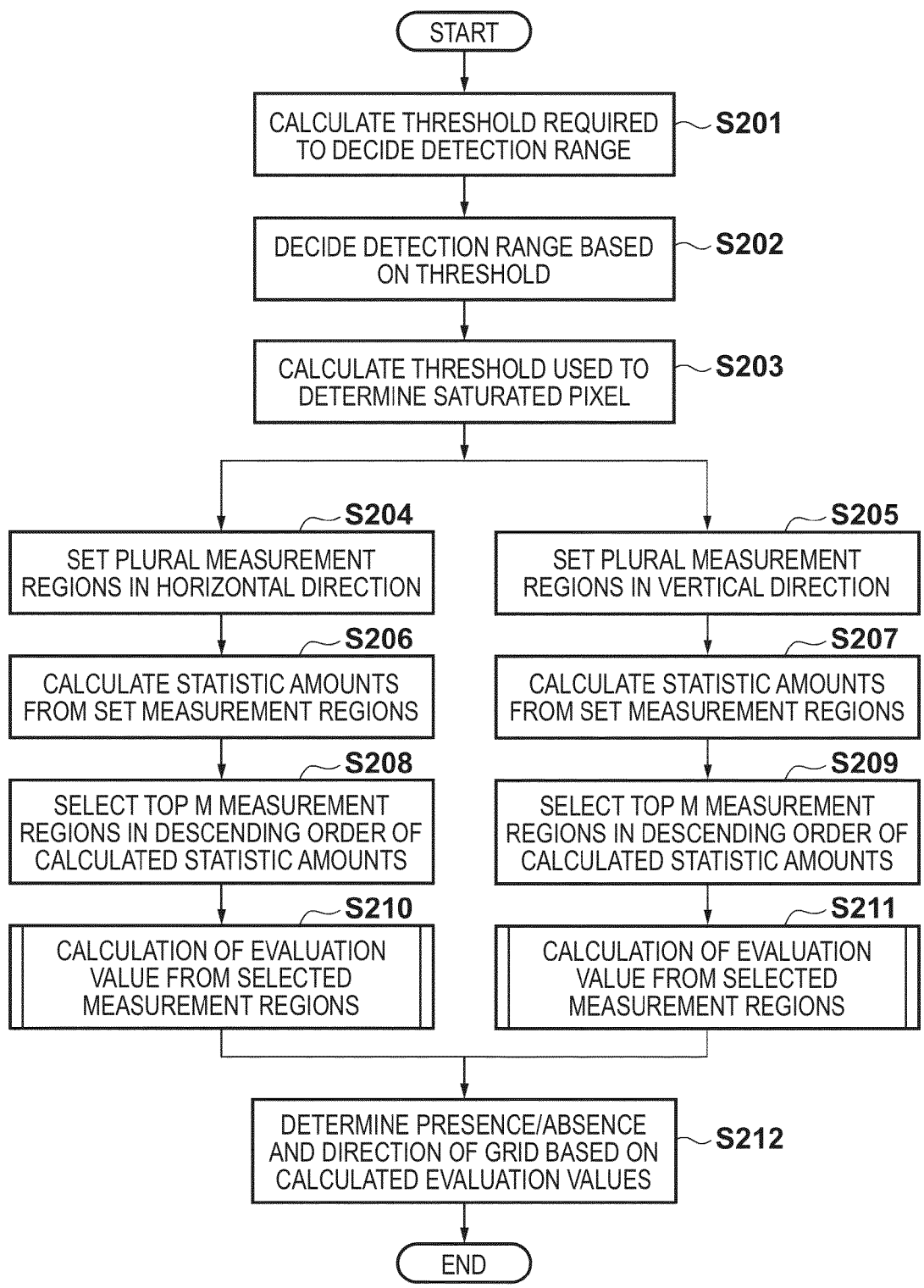
FIG. 2 is a flowchart showing the processing sequence of an image analysis unit according to the embodiment.

Next, in step S212 in FIG. 2, the determination unit 123 compares an evaluation value $E_h$ as $E_{max}$ in the horizontal direction calculated from the measurement regions set in the horizontal direction, and an evaluation value $E_v$ as $E_{max}$ in the vertical direction calculated from the measurement regions set in the vertical direction. Then, the determination unit 123 determines the presence/absence of the grid 150 and a direction of a grid line corresponding to the grid 150 from this comparison result, and outputs a result. When the evaluation value $E_h$ is larger than the evaluation value $E_v$ and exceeds a predetermined threshold TH, the determination unit 123 determines that an image includes the grid line in the horizontal direction, and outputs the grid frequency $F_r$ calculated from the measurement regions set in the horizontal direction together.

On the other hand, when the evaluation value $E_v$ is larger than the evaluation value $E_h$ and exceeds the predetermined threshold TH, the determination unit 123 determines that an image includes the grid line in the vertical direction, and outputs the grid frequency $F_r$ calculated from the measurement regions set in the vertical direction together. Otherwise, the determination unit 123 determines that an image does not include any periodic signal corresponding to the arrangement of the grid, that is, any periodic signal caused by the grid.

Note that the threshold TH is that required to evaluate the significance of the evaluation value, and can be empirically set based on statistic properties of evaluation values $E_i$ calculated from image data obtained when the grid is arranged. Note that in this embodiment, the threshold TH is set to be, for example, 50.

The embodiment has been explained. However, the present invention is not limited to the aforementioned embodiment, and various modifications and changes can be made within the scope of the invention.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-020832, filed Feb. 5, 2013, which is hereby incorporated by reference herein in its entirety.

What is claimed is:

1. An image analysis apparatus for detecting a periodic signal corresponding to an arrangement of a grid, which is required to reduce scattered radiation components from an object, from an image obtained by radiation imaging using the grid, said apparatus comprising:
   a processor; and
   memory,
   the processor and the memory being operatively coupled to function as:
      a setting unit configured to set a plurality of regions on the image;
      an obtaining unit configured to obtain statistical information of pixel values corresponding to each of the plurality of regions of the image based on the image;
      a selection unit configured to select at least one measurement region from the plurality of regions based on the statistical information; and
      a detection unit configured to detect a spatial frequency corresponding to the periodic signal, based on the selected measurement region.

2. The apparatus according to claim 1, wherein the processor and the memory further function as a detection range decision unit configured to decide a detection range required to detect the periodic signal from the image, and
   wherein said setting unit sets the plurality of regions from the detection range.

3. The apparatus according to claim 2, wherein the detection range includes a radiation irradiation region in which the object is irradiated with a radiation.

4. The apparatus according to claim 1, wherein the processor and the memory further function as a saturated pixel determination unit configured to determine a saturated pixel, a pixel value of which is saturated, in image data of each measurement region set by said setting unit by comparing the pixel value with a threshold, and
   wherein said obtaining unit obtains the statistical information based on image data except for the saturated pixel.

5. The apparatus according to claim 1, wherein said obtaining unit obtains, as the statistical information, at least one of an average value, a mode, an order statistic value, a sum total value, a variance, and a standard deviation.

6. The apparatus according to claim 1, wherein said selection unit selects the measurement region based on a value indicated by the statistical information.

7. The apparatus according to claim 1, wherein said setting unit sets a plurality of measurement regions arranged in a first direction of the image and a plurality of measurement regions arranged in a second direction perpendicular to the first direction, and said selection unit selects, using the statistical information, at least one measurement region from the plurality of measurement regions in the first direction, and further selects at least one measurement region from the plurality of measurement regions in the second direction.

8. The apparatus according to claim 1, wherein the detection unit detects the periodic signal from the image, based on a comparison between a peak of a power spectrum included in image data of the selected measurement region and power spectra around the peak, wherein said detection unit comprises:
 a filtering unit configured to apply filtering to image data of the selected measurement region;
 a power spectrum calculation unit configured to calculate a the power spectrum from the filtered image data of the measurement region;
 an evaluation value calculation unit configured to calculate an evaluation value used to judge the presence/absence of the periodic signal corresponding to the arrangement of the grid based on the peak of the calculated power spectrum; and
 a determination unit configured to determine the presence/absence of the periodic signal and a direction of the arrangement of the grid using the evaluation value, and
wherein the filtering unit, the power spectrum calculation unit, the evaluation value calculation unit, and the determination unit are implemented using the processor and the memory.

9. The apparatus according to claim 8, wherein said determination unit determines the presence/absence of the periodic signal and a direction of the arrangement of the grid using an evaluation value of measurement regions in a first direction of the image and an evaluation value of measurement regions in a second direction perpendicular to the first direction.

10. The apparatus according to claim 8, wherein the processor and the memory further function as a clipping unit configured to set image data used in the filtering, wherein when image data of the selected measurement region includes a saturated pixel, a pixel value of which is saturated, said clipping unit converts the pixel value of the saturated pixel to a fixed value, and sets the fixed value as image data used in the filtering, and when image data of the selected measurement region does not include the saturated pixel, said clipping unit sets pixel values of respective pixels of the image data as image data used in the filtering.

11. The apparatus according to claim 8, wherein said filtering unit uses a high-pass filter which passes through frequencies not less than a predetermined frequency in the filtering.

12. The apparatus according to claim 11, wherein the predetermined frequency is decided using the number of arranged lines of the grid per unit length and a pixel pitch of said detecting unit used in the radiation imaging.

13. The apparatus according to claim 8, wherein when there are a plurality of predetermined frequencies, said filtering unit uses a lowest frequency in the filtering.

14. The apparatus according to claim 8, wherein said evaluation value calculation unit calculates the evaluation value using a ratio between a peak of the power spectrum and power spectra around the peak.

15. The apparatus according to claim 14, wherein said evaluation value calculation unit calculates the evaluation value further using a ratio between a peak present in a frequency band separated from the peak by not less than a predetermined frequency and power spectra around the peak present in the frequency band separated by not less than the frequency.

16. A radiation imaging apparatus comprising:
 an image analysis apparatus according to claim 1; and
 an image processing unit configured to execute reduction processing of the periodic signal detected by said image analysis apparatus, wherein the image processing unit is implemented using the processor and the memory.

17. The apparatus according to claim 16, wherein the processor and the memory further function to control a display to display an image which has undergone the reduction processing of the periodic signal by said image processing unit.

18. An image analysis method of an image analysis apparatus for detecting a periodic signal corresponding to an arrangement of a grid, which is required to reduce scattered radiation components from an object, from an image obtained by radiation imaging using the grid, the method comprising:
 a setting step of setting a plurality of regions on the image;
 an obtaining step of obtaining statistic information of pixel values corresponding to each of the plurality of regions of the image based on the image;
 a selection step of selecting at least one measurement region from the plurality of regions based on the statistic information; and
 a detection step of detecting a spatial frequency corresponding to the periodic signal, based on the selected measurement region.

19. A non-transitory computer-readable storage medium storing a program for controlling a computer to function as an image analysis apparatus for detecting a periodic signal corresponding to an arrangement of a grid, which is required to reduce scattered radiation components from an object, from an image obtained by radiation imaging using the grid, the apparatus comprising:
 a setting unit configured to set a plurality of regions on the image;
 an obtaining unit configured to obtain statistic information of pixel values corresponding to each of the plurality of regions of the image based on the image;
 a selection unit configured to select at least one measurement region from the plurality of regions based on the statistic information; and
 a detection unit configured to detect a spatial frequency corresponding to the periodic signal, based on the selected measurement region.

20. An image analysis apparatus for detecting a periodic signal corresponding to an arrangement of a grid, which is required to reduce scattered radiation components from an object, from an image obtained by radiation imaging using the grid, said apparatus comprising:
 setting means for setting a plurality of regions on the image;
 obtaining means for obtaining statistical information of pixel values corresponding to each of the plurality of regions of the image based on the image;
 selection means for selecting at least one measurement region from the plurality of regions based on the statistical information; and detection means for detecting a spatial frequency corresponding to the periodic signal, based on the selected measurement region.

21. An image analysis apparatus for detecting a periodic signal corresponding to an arrangement of a grid, which is required to reduce scattered radiation components from an object, from an image obtained by radiation imaging using the grid, said apparatus comprising:

a processor; and memory, the processor and the memory being operatively coupled to function as:

a setting unit configured to set a plurality of regions on the image;

an obtaining unit configured to obtain statistical information of pixel values corresponding to each of the plurality of regions of the image based on the image;

a selection unit configured to select at least one measurement region from the plurality of regions based on the statistical information; and a determination unit configured to, based on the selected measurement region, determine at least one of whether the periodic signal is included in the image data, and a direction of the arrangement of the grid.

22. An image analysis method of an image analysis apparatus for detecting a periodic signal corresponding to an arrangement of a grid, which is required to reduce scattered radiation components from an object, from an image obtained by radiation imaging using the grid, the method comprising:

a setting step of setting a plurality of regions on the image;

an obtaining step of obtaining statistical information of pixel values corresponding to each of the plurality of regions of the image based on the image;

a selection step of selecting at least one measurement region from the plurality of regions based on the statistical information; and a determination step of, based on the selected measurement region, determining at least one of whether the periodic signal is included in the image data, and a direction of the arrangement of the grid.

* * * * *